United States Patent
Tate

(10) Patent No.: US 6,170,088 B1
(45) Date of Patent: Jan. 9, 2001

(54) ARTICLE OF CLOTHING WITH ATTACHABLE MAGNETIC BALL MARKER

(76) Inventor: John R. Tate, 11621 Markon Dr., Garden Grove, CA (US) 92841

( * ) Notice: Under 35 U.S.C. 154(b), the term of this patent shall be extended for 0 days.

(21) Appl. No.: 09/426,786

(22) Filed: Oct. 22, 1999

Related U.S. Application Data

(63) Continuation-in-part of application No. 09/187,684, filed on Nov. 5, 1998, now Pat. No. 5,996,116, and a continuation-in-part of application No. 09/336,072, filed on Jun. 18, 1999.

(51) Int. Cl.[7] .......................................... A42B 1/24
(52) U.S. Cl. ....................... 2/209.13; 2/195.1; 2/200.1; 2/12; 2/425
(58) Field of Search .......................... 2/12, 209.13, 422, 2/425, 195.1, 200.1

(56) References Cited

U.S. PATENT DOCUMENTS 4,130,950 * 12/1978 Bazzle et al. ........................... 36/127
5,364,094 * 11/1994 Mustison .............................. 273/32 A

* cited by examiner

Primary Examiner—Bibhu Mohanty

(74) Attorney, Agent, or Firm—Charles H. Thomas

(57) ABSTRACT

A ferrous object is attached to or embedded within an article of golf clothing so that it is subject to the force of magnetic attraction of a magnet in a ball marker. A magnetic ball marker according to the invention has a body that can be stamped, painted, machined, or otherwise provided with surface embellishments, such as tournament logos, golf course crests, corporate logos, and other visual indicia that are favored by golfers. Unlike conventional golf ball markers, however, a ball marker according to the invention is provided with a thin, flat, permanent magnet that is attached to or embedded within the body of the ball marker. When the ball marker is moved into the proximity of an article of golf clothing modified according to the invention by the incorporation of a ferrous object therein, the ball marker will be attracted to the ferrous object and will cling to the article of golf clothing until purposely removed therefrom. The invention has particular applicability to golf headgear, such a hats and visors. The ferrous objects employed may be configured as thin metal sheets, discs, wafers, or strips attached to or embedded within the bill or a golf hat or visor. The magnet ball marker of the invention is then simply placed in contact with or even in near proximity to the area of the hat at which the ferrous object has been permanently attached. The magnetic ball marker will thereupon cling to the article of golf clothing until removed therefrom for use.

17 Claims, 8 Drawing Sheets

ARTICLE OF CLOTHING WITH ATTACHABLE MAGNETIC BALL MARKER

The present invention is a continuation in part of U.S. application Ser. No. 09/187,684 now U.S. Pat. No. 5,996,116, filed Nov. 5, 1998, presently pending, and also a continuation in part of U.S. application Ser. No. 09/336,072, filed Jun. 18, 1999, presently pending.

BACKGROUND OF THE INVENTION

1. Field of the Invention

The present invention relates to a system for releasably securing a golf ball marker to a fabric golf accessory, such as a golf hat, a sun visor, a golfing glove, or a towel, and an improvement to a golf accessory by the combination of a magnetic golf ball marker therewith.

2. Description of the Prior Art

Golf ball markers have been used for many, many years in order to mark the position of a golf ball on a fairway or green during a game of golf engaged in by competitive players. Golf ball markers are typically formed as small, disc-shaped structures, usually fabricated from metal. Conventional golf ball markers are often stamped from a ferrous material, usually steel or iron. Some conventional golf ball markers have a plain, unadorned appearance, although in more competitive golfing circles ball markers having surface embellishments on their faces are now widely utilized. Conventional ball markers may include the sculptured and/or painted reproductions of a golf course or tournament logo, a country club insignia, a corporate or university logo or insignia, or more personalized surface embellishments. Whatever the particular adornment adopted for a golf ball marker by a player, more often than not the player is proud to display the ball marker, since it is frequently indicative of courses or tournaments in which the player has participated or otherwise attests to the players experience, competence, or interest in participation in the game of golf.

While a player may be happy to display a ball marker, in conventional use, golf ball markers offer only a limited opportunity for such display. More often, when a golfer's ball lies in the field of play, the ball marker is typically carried in the golfer's pocket, and is thus concealed from view. Furthermore, when a golf ball marker is carried in a player's pocket, the player is often forced to dig and fumble through the contents of the pocket in order to retrieve it. Golf ball markers have similar sizes and shapes to coins of currency, which are often carried in the same pocket. A golf ball marker therefore cannot be separated easily from the other contents of the pocket by the sense of touch. The retrieval of a golf ball marker for use thereby creates a source of annoyance and distraction to the golfer.

Systems for enhancing the convenience of access and extent of display of golf ball markers have been devised in the past. For example, golf ball markers may be releasably mounted by means of magnets in golf divot tools that are utilized to repair divots and spruce up golf greens. Golf divot tools may be formed with one or more shallow, disc-shaped recesses therein at the bottom of which a flat slab of magnetic material is permanently secured. A ferrous ball marker formed of steel or soft iron may then be releasably held in position in the recess or tray of a golf divot tool by the magnetic force of attraction of the magnetic material. As a consequence, when the divot repair tool is utilized the ball marker is conveniently accessible and is also displayed for all to see.

U.S. Pat. Nos. 5,295,683 and 5,305,999 disclose and describe divot tools of different configurations in which golf ball markers are releasably mounted by the force of magnetic attraction. Also, the tool of U.S. Pat. No. 5,305,999 includes a clip that may be attached to the belt, cap, shoe, pocket, or golf bag of a golfer. As a consequence, when the divot tool is carried in this manner the golf marker is more easily retrieved and is also prominently displayed. Nevertheless, since divot tools themselves are used only on limited occasions, the opportunities for conveniently retrieving a golf ball marker by releasably mounting it on a divot tool are somewhat limited.

In prior U.S. applications Ser. Nos. 09/187,684 and 09/336,072, both of which are incorporated herein in their entireties by reference, several systems are described in which magnets are embedded in or attached to articles of clothing. For example, those prior applications describe systems in which magnets are attached to or embedded in the bill of a golf hat or visor. Also, U.S. patent application Ser. No. 09/336,072 describes systems in which a magnet may be placed within a patch that is affixed to an article of golf clothing, such as a hat. An iron or steel golf ball marker brought into the proximity of the magnets in any of these articles of clothing will be attracted to the magnets that are secured to the golf clothing or other golf accessory. The golf ball marker may thereby be carried in open display and in an easily accessible manner.

SUMMARY OF THE INVENTION

I have since envisioned and developed a novel variation of the systems described in my prior U.S. patent applications Ser. Nos. 09/187,684 and 09/336,072. More specifically, according to the present invention an object formed of a ferrous material, such as a thin, flat iron or steel disc or plate, is secured in position relative to an article of golf clothing or other golf accessory. A golf ball marker is formed which includes a magnet in its structure. The ball marker must include some structure which can be stamped, painted, imprinted, or otherwise emblazoned with crests, logos, and other indicia that are preferred and accepted by golfers. However, a magnet is permanently affixed to or incorporated into the structure of an otherwise conventional golf ball marker.

The magnetic ball marker system of the invention has the advantage that the ball marker will be attracted to the ferrous object in the article of golf clothing or the golf accessory. The ball marker will thereby cling to the external surface of the article of golf clothing or the golf accessory due to the force of magnetic attraction between the magnet incorporated into the structure of the golf ball marker and the iron or steel object that is incorporated into or attached to the structure of the golf clothing or golf accessory.

The object formed of a material attracted by the force of magnetism is incorporated into or attached to the article of golf clothing or golf accessory. This object may be either located beneath a fabric sheet-like surface on the article or it may be mounted externally on the article. If the iron or steel object is concealed from view by an overlying layer of fabric, the fabric must be thin enough so that the magnet on the ball marker can be moved sufficiently close to the iron or steel object. This is typically not a problem in the case of golf clothing and golf accessories that include a layer of fabric, such as golf hats, golf shirts, golf visors, golf gloves, etc. The overlying layer of fabric is typically no greater than about three-sixteenths of an inch in thickness, and often is considerably thinner.

In other applications, the ferrous metal object in the article of golf clothing or other golf accessory may be positioned externally. For example, the ferrous object may be formed as a thin iron or steel sheet or plaque that is fastened externally atop the bill of a golf cap or visor. When located on the exposed surface of an article of golf clothing or other golf accessory, the ferrous object will typically have a decoration and/or surface ornamentation. When the ferrous object is externally mounted, such as atop the bill of a golf cap or visor, the ball marker will be attracted to and directly contact the ferrous object that is secured to the article of golf clothing.

The ball marker retention system of the invention involves releasably positioning a golf ball marker into which a magnet has been incorporated on the exposed fabric surface of a golf accessory, such as an article of golf clothing. For example, golf ball markers may be prominently displayed on golf hats, caps, sun visors, golfing gloves, golf towels, golf bags, and other golfing accessories that are formed of fabric. The system for retaining magnetic golf ball markers in position in this manner involves the incorporation of a flat strip or slab of material attracted by magnetism into the fabric structure of an article of golf clothing or some other golf accessory.

According to some embodiments of the invention, one or more slabs, strips, or other shapes of ferrous material are mounted beneath the exposed surface of the fabric of an article of golf wear or a golfing accessory and secured out of sight. Nevertheless, the force of magnetic attraction exerted by the magnet on the golf ball marker acts through the fabric material with sufficient strength so that the magnetic golf ball marker will be held in position against the exposed surface of the fabric while the ferrous material which is attracted by the magnetic field exerted by the ball marker remains concealed from view on the inside, hidden surface of the fabric.

By utilizing the system of the invention, golf ball markers will adhere to articles of clothing and can be held in place by the force of magnetic attraction with a sufficient strength so that they will not become dislodged therefrom accidentally. To the contrary, the magnetic field exerted by the magnet of the ball marker through the cloth structure is sufficient to hold a ball marker bearing a magnet firmly in position until and unless the user purposefully overcomes that force and pulls the ball marker clear from the article of clothing so that the ferrous material embedded therein is beyond the influence of the magnetic field of the magnet in the ball marker.

In one broad aspect the present invention may be considered to be an improvement in an article of golf clothing having at least one layer of fabric with a visually exposed side and an opposite concealed side. The improvement is comprised of at least one flat object formed of ferrous material secured in position to the layer of fabric at a selected, fixed location thereon, and a ball marker formed of a body and a magnet permanently secured to the body. The body may be formed of a nonmagnetic material. When placed near the fixed location on the layer of fabric, the ball marker is magnetically held to the object of ferrous material by the force of magnetic attraction between the magnet of the ball marker and the object of ferrous material.

The term fabric, as used herein, is to be construed in its broadest sense of any thin, expansive, flexible, or supple material of the type typically utilized in the construction of golf clothing and other golfing accessories. The term fabric should be construed as encompassing not only woven cloth textiles, but also other flexible, thin, expansive materials such as leather, plastic sheet material, and felt, for example.

In one preferred embodiment of the invention, the fabric golf accessory is a hat that has a bill formed of a stiff, substantially flat interior core. The core of the bill is encapsulated within a cloth fabric covering. The object formed of ferrous material may be glued or sewn into position atop the stiff, interior core forming the bill of the cap, and covered by the cloth fabric forming the cap. Alternatively, it may be located within a cavity defined in the core of the cap. In still another arrangement, the object of ferrous material may be attached to the outer, exposed fabric surface on the bill of the cap.

The magnet incorporated into the structure of the ball marker may be a flexible sheet or layer of rubber with magnetized ferrous particles of iron or iron oxide embedded therein. Preferably, however, the magnet is a thin, flat slab of magnetized iron or steel. The magnetic slab may be formed as a disc, a rectangle, or any other geometric shape.

In another broad aspect, the invention may be considered to be a golf ball marker comprising a body having an exposed surface bearing an indicia, and a magnet permanently secured to the body so as to not obscure the indicia thereon. Such a magnetic ball marker will be attracted to and cling to an article of golf clothing having an object formed of ferrous material embedded therein or attached thereto.

The magnetic ball marker, the article of golf clothing, and the ferrous object attached to the article of golf clothing form a unique combination according to the invention. However, the magnetic ball marker by itself is advantageous in other ways as well. A golfer may pick up the magnetic ball marker of the invention without bending over to do so by merely touching the iron or steel head of a golf club or putter onto the magnetic marker to lift the marker from a fairway or green. Also, a magnetic ball marker may be carried in the golfer's pocket, but can be readily separated from loose change that is also carried in the golfer's pocket by merely inserting an iron or steel object, such as a key or golf divot tool into the golfer's pocket. The ball marker will attach itself to such a ferrous object so that it can be easily separated from loose change in the golf's pocket and withdrawn for use.

In still another aspect the invention may be considered to be a combination of an article of clothing, a patch including a shallow tray, an object formed of a ferrous material, a layer of adhesive, and a magnetic golf ball marker. The article of clothing includes a layer of flexible fabric material having an exposed side and an opposite concealed side. The shallow tray of the patch has a floor, and walls projecting outwardly from the floor to define a laterally enclosed cavity. The patch has an outwardly facing attachment surface surrounding the cavity. The object formed of ferrous material is located within the cavity. The layer of adhesive is interposed between the attachment surface of the patch and the concealed surface of the fabric material, thereby joining the patch to the layer of fabric material with the cavity enclosed therebetween and with the object formed of ferrous material trapped between the shallow tray and the concealed side of the layer of fabric material. The golf ball marker has a magnet permanently attached thereto. When the ball marker is positioned at the exposed surface of the layer of flexible fabric material proximate the object formed of ferrous material, the magnet exerts a force of attraction through the layer of fabric material. This force holds the golf ball marker in contact with the exposed surface of fabric material proximate the object of ferrous material.

In still another aspect the invention may be considered to be a method of carrying a golf ball marker in open display on a fabric golf accessory comprising: securing an object of material attracted by magnetism to a layer of fabric of a golf accessory, and placing a golf ball marker formed of a magnetically inert body and a permanent magnet permanently secured to that body near the object of material attracted by magnetism. A magnetic field produced by the magnet on the golf ball marker draws the golf ball marker toward the object attracted by magnetism and holds it relative thereto when the golf ball marker is moved into the vicinity of the object of material attracted by magnetism. There it will remain until an opposing force stronger than the magnetic field dislodges the golf ball marker from the layer of fabric.

The invention may also be considered to be an improvement to a golf accessory formed with an exposed layer of fabric. The improvement is comprised of a flat, thin object formed of ferrous material attached to and concealed by the exposed layer of fabric at a selected location thereon. The improvement also includes a detached golf ball marker including a permanent magnet permanently incorporated therein. The magnetic force of attraction of the magnet acts through the exposed layer of fabric to hold the golf ball marker against the exposed layer of fabric at the selected location when moved into proximity thereto.

In still another aspect the invention may be considered to be an improvement to an article of golf clothing comprising a flat, thin object of ferrous material attached to the article of clothing at a selected location thereon. The article of golf clothing includes a layer of nonferrous sheet material that conceals the object of ferrous material from view at the selected location. The improvement also includes a detached golf ball marker that has a nonmagnetic body and a magnet permanently attached to the nonmagnetic body. The magnet draws the golf ball marker toward the object of ferrous material and holds the golf ball marker against the layer of nonferrous sheet material when moved into proximity to the selected location.

In still another aspect the invention may be considered to be, in combination, an article of golf clothing formed of a flexible material having an exterior surface, a thin wafer of ferrous material permanently attached to the article of clothing beneath the exterior surface of the flexible material, and a golf ball marker formed of a body with a magnet permanently attached to the body. The golf ball marker is placed in contact with the exterior surface of the flexible material so that the magnet exerts a magnetic field that acts through the flexible material. The golf ball marker adheres to the article of clothing on the exterior surface of the flexible material when moved into proximity to the wafer of ferrous material unless dislodged therefrom by a force stronger than the magnetic field.

In still another aspect the invention may be considered to be the combination of a golf accessory constructed of fabric having an exterior surface, a thin ferrous object permanently secured within the confines of the fabric, and a golf ball marker formed of a magnetically inert body having a magnet permanently secured thereto. The golf ball marker is located upon the exterior surface of the fabric. The magnet of the golf ball marker exerts a force of magnetic attraction, whereby the ball marker is attracted toward the ferrous object. The ball marker remains secured in place on the exterior surface of the fabric when moved into proximity to the ferrous object until removed with a force that overcomes the force of magnetic attraction.

The invention may be described with greater clarity and particularity by reference to the accompanying drawings.

DESCRIPTION OF THE EMBODIMENTS

Figure 1:
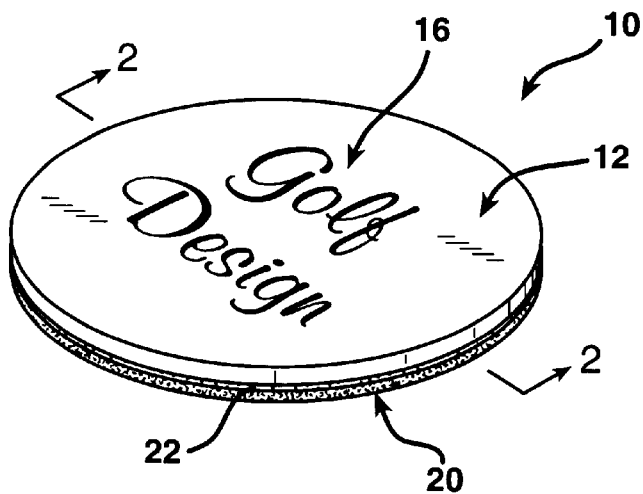
FIG. 1 is a perspective view of one preferred embodiment of a golf ball marker constructed according to the invention.
Figure 2:
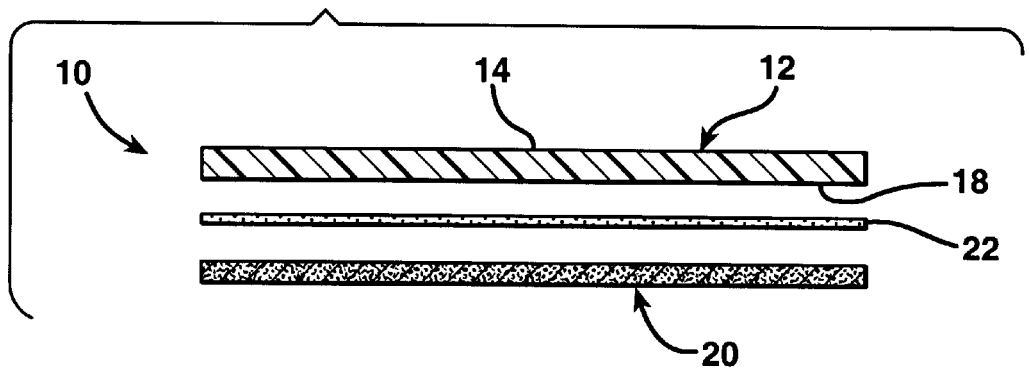
FIG. 2 is a side elevational exploded view of the golf ball marker of FIG. 1.
Figure 3:
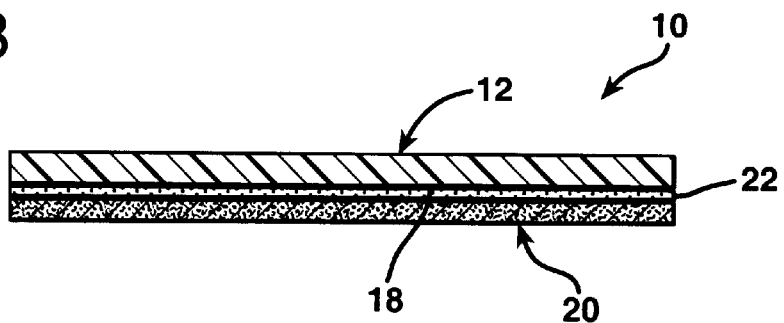
FIG. 3 is a side elevational view of the golf ball marker of FIG. 1 is its finished condition.

FIGS. 1, 2, and 3 illustrate one embodiment of a golf ball marker 10 constructed according to the invention. The golf ball marker 10 includes a flat, disc-shaped slab 12 of nonferrous material, such as brass or plastic. The disc-shaped slab 12 has an exposed surface 14 thereon bearing an indicia indicated generally at 16 and a concealed surface 18. The indicia may be in the form of a raised embossment; an indented stamping; a painted symbol, logo, or design; or any combination of different types of indicia utilized on conventional golf ball markers.

The golf ball marker 10 also includes a flat, thin disc-shaped magnet 20 which is coextensive in area with the nonmagnetic slab 12. The magnet 20 is permanently attached to the concealed surface 18 of the flat slab 12 by a thin layer of adhesive indicated at 22. The adhesive 22, when compressed between the nonmagnetic slab 12 and the magnet 20 spreads out to form a thin film extending across the entire interface between the concealed surface 18 of the nonmagnetic slab 12 and the magnet 20. The adhesive layer 22 is preferably an adhesive material that is designed for establishing a very tight adhesive bond between two metals. The layer of adhesive 22 may, for example, be formed of a drop of Locktite adhesive, manufactured by 3M Corporation located in Minneapolis, Minn.

The flat slab 12 may, for example, be formed of brass or stainless steel covered with brass. Alternatively, it may be formed of plastic. The slab 12 could be formed of iron or steel but is preferably formed of a material insensitive to magnetism, so that the ball marker, when moved into position proximate an article formed of ferrous material, will magnetically adhere thereto with the magnet 20 facing the ferrous object. As a consequence, the indica 16 will face outwardly and will be visible. Indeed, if the golf ball marker 10 is moved into the proximity of an object formed of a ferrous material with the exposed surface 14 of the magnetically insensitive slab 12 facing the ferrous object, the ball marker 10 will automatically flip itself over so that the magnet 20 faces the ferrous object and so that the exposed surface 14 bearing the indicia 16 faces outwardly and is clearly visible.

Preferably, the ball marker 10 has a diameter of either three-quarters of one inch (19 millimeters) or one inch (25.4 millimeters). The magnet 20 preferably has a thickness of about 0.02 inches (about 5 millimeters), while the entire structure of the ball marker 10 is preferably between 0.031 and about 0.034 inches in thickness (about 0.79–0.86 millimeters). The slab 12 preferably has a thickness of between about 0.29–0.32 inches (0.74–0.81 millimeters).

Figure 4:
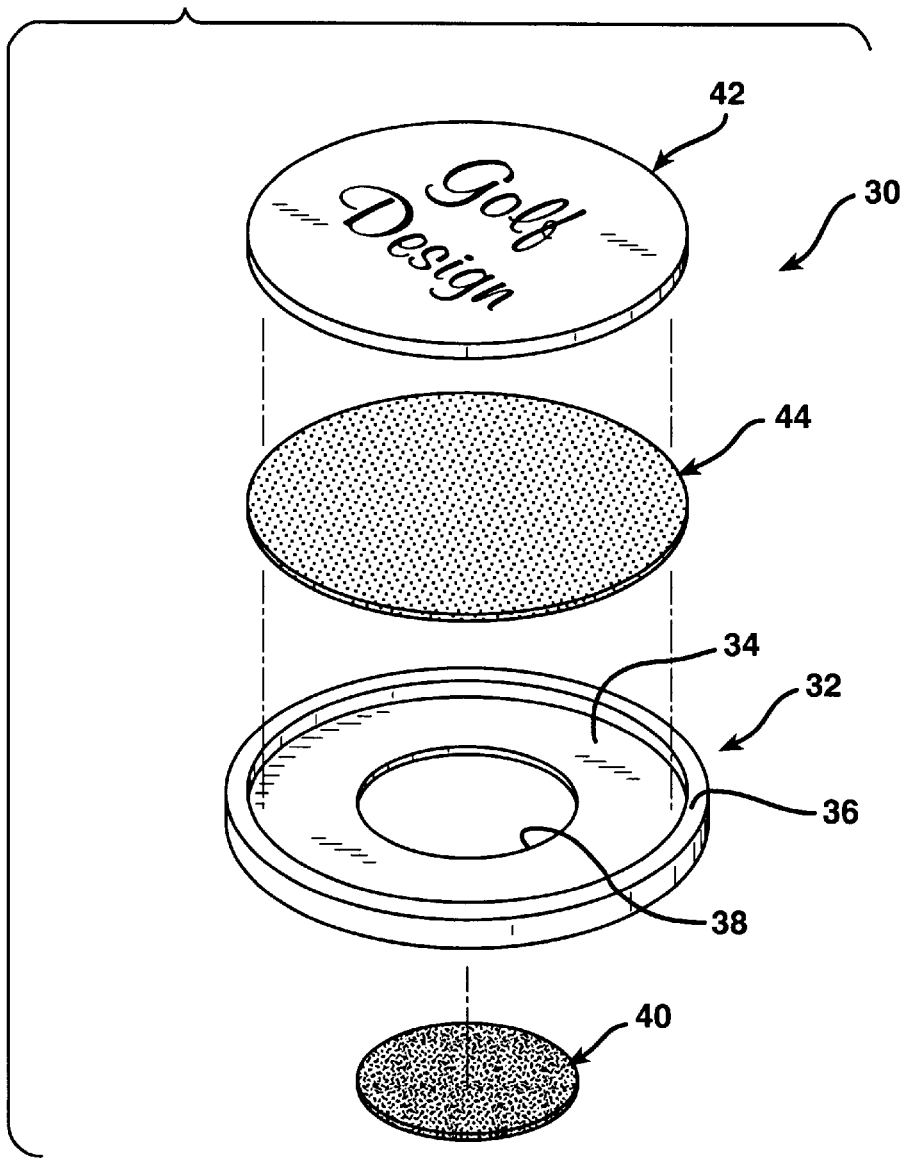
FIG. 4 is a exploded perspective view of another preferred embodiment of a golf ball marker according to the invention.
Figure 5:
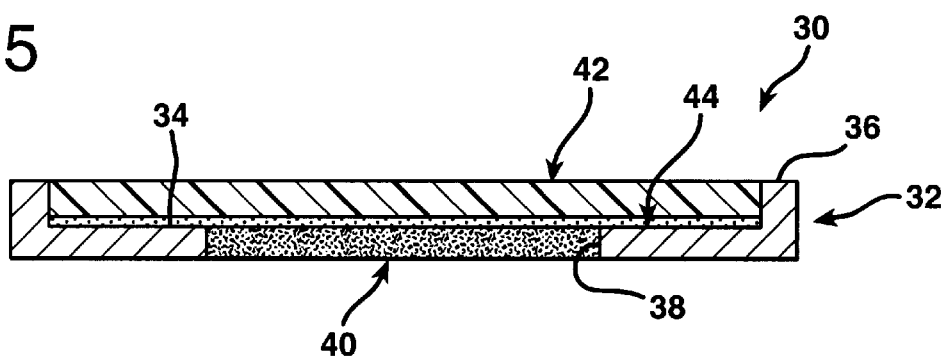
FIG. 5 is a side elevational view of the golf ball marker of FIG. 4.

FIGS. 4 and 5 illustrate a different embodiment of a magnetic golf ball marker according to the invention. The golf ball marker 30 is comprised of a frame 32, a magnet 40, and a visually attractive body such as a disc-shaped hologram or decal 42, all secured together by a layer of adhesive, indicated at 44. The frame 32 has a circular periphery and forms a tray having a floor 34 surrounded by an annular peripheral rim 36. A circular, central opening 38 is defined in the floor 34. The decal or hologram 42 is a flat slab of nonferrous material that is seated in the tray formed by the frame 32 and is surrounded by the peripheral rim 36.

The frame 32 has an outer diameter of either 0.75 inches or 1.00 inches. These are the standard sizes for golf ball markers. The frame 32 is between about 1.2 and about 1.45 millimeters in thickness measured at its periphery at the rim 36. The floor 34 has a thickness of about 0.6 millimeters, and the peripheral rim 36 rises a distance of about 0.6 millimeters above the floor 34. The magnet 40 has a disc-shaped configuration and is preferably about twelve millimeters in diameter and about 0.8 millimeters thick (0.031 inches) for a frame 32 of one inch outer diameter. For a frame 32 that is 0.75 inches in diameter the magnet 40 should be about 0.5 inches in diameter and about 0.6 millimeters thick (0.024 inches). The thickness of the magnet 40 should be proportional to its diameter so that it will not break easily during construction of the ball marker 30.

The magnet 40 is formed of a nickel-ferrous-boron alloy which is permanently magnetized to exert a considerable magnetic force for its size. The decal or hologram 42 may be formed of paper or plastic and preferably has a thickness of about 0.2 millimeters. The adhesive layer 44 may be the Locktite adhesive previously described and exerts a strong adhesive bond with the floor 34, the undersurface of the decal or hologram 42, and the upper surface of the magnet 40.

The magnet 40 is located and fits snugly within the central, circular opening 38 of the floor 34 of the tray of the frame 32. The adhesive layer 44 tightly bonds the magnet 40 to the underside of the decal or hologram 42, and also bonds the underside of the decal or hologram 42 tightly to the annular upwardly facing surface of the floor 34.

Figure 6:
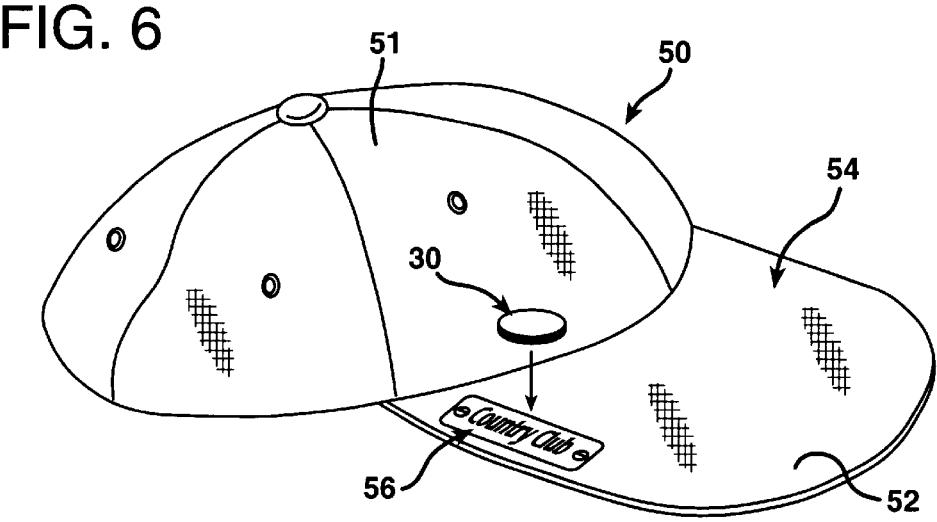
FIG. 6 is a perspective view illustrating an improved article of golf clothing according to the invention.

FIG. 6 illustrates a golf accessory, namely an article of golf clothing. More specifically, FIG. 6 illustrates an article of golf headgear which is a golf hat 50 that is constructed with improvements according to the invention. The golf hat 50 is formed with an exposed layer fabric 52 on the hat bill 54. The hat 50 also has a thin object formed of ferrous material, which in the embodiment illustrated in FIG. 6, is a thin, rectangular-shaped steel plate 56 having a raised rim and raised lettering and simulated screw heads thereon as illustrated in greater detail in FIG. 7. The thin steel plate 56 may be attached to the outer, exposed surface of the fabric layer 52 by means of an adhesive and/or by depending spikes or fastening prongs, or by any other conventional means that permanently attaches the steel plate 56 in a fixed position on the exposed side of the fabric layer 52 of the hat bill 54.

The ball marker 30 shown in FIG. 6 may be of the type illustrated in detail in FIGS. 4 and 5. It is to be understood that other ball markers according to the invention may also be employed in combination with the hat 50 and iron or steel plate 56. For example, the ball marker 10 shown in FIGS. 1–3 could alternatively be utilized as shown in FIG. 6, in place of the ball marker 30. In any event, the golf ball marker employed in the manner illustrated in FIG. 6 is formed of a body with a magnet permanently secured to the body.

To utilize the invention shown if FIG. 6, a golfer merely picks up the ball marker 30 from a position on the green or fairway at which it has been placed, and places it onto his or her hat bill 54 generally near the location of the steel plate 56. When the magnetic ball marker 30 is placed near the selected, fixed location at which the steel plate 56 is secured to the layer of fabric 52, it is held to the steel plate 56 by the force of magnetic attraction between the magnet 40 of the ball marker 30 and the steel plate 56. The force of magnetic attraction exerted by the magnet 40 is sufficient to pull the golf ball marker 30 onto the steel plate 56 even if the marker 30 is initially placed in direct contact with the exposed surface of the fabric layer 52, off to one side of the steel plate 56, as long as it is placed reasonably near the steel plate 56. The force of magnetic attraction of the magnet 40 in the magnetic ball marker 30, coupled with the light weight of the ball marker 30, will draw the ball marker 30 onto the steel plate 56 from a distance of one inch or more.

Figure 9:
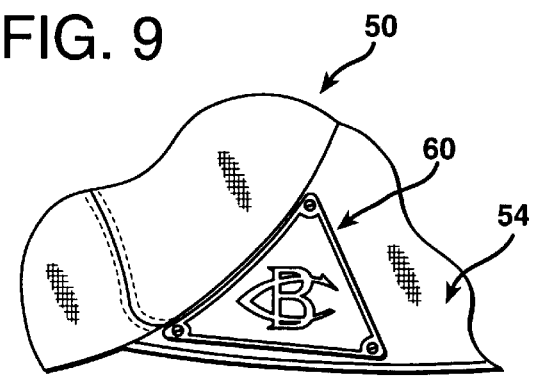
FIG. 9 is a perspective detail illustrating still another article formed of ferrous material affixed to a golf hat according the invention.
Figure 8:
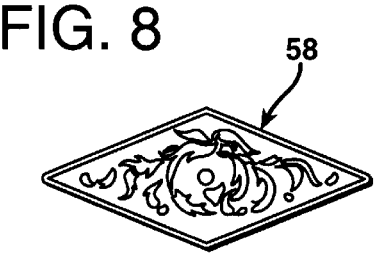
FIG. 8 is a plan detail illustrating an alternative embodiment of the ferrous object of FIG. 7.
Figure 10:
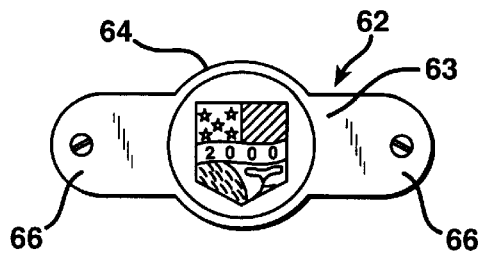
FIG. 10 illustrates still another alternative embodiment of an article formed of ferrous material and used in a combination according to the invention.

FIGS. 8, 9, and 10 illustrate other forms of objects 58, 60, and 62, respectively, suitable for use in attracting a magnetic golf ball marker and suitable for use in combination with an article of golf clothing. The objects 58 and 60 are formed of a ferrous material, preferably a thin, flat sheet or strip of iron or stainless steel coated to prevent rusting. Preferably, the objects 58, 60, and 62 are decorated with some surface ornamentation, which may include a tournament logo, a golf or country club logo, a university crest, or some other surface embellishment that is visually attractive to a golfer. All of the objects 58, 60, and 62 are designed to be secured atop the visually exposed side of the layer of fabric 52 on the upper surface of the hat bill 54, or upon some other fabric layer of a golf hat or other golf accessory.

FIG. 8 illustrates a diamond-shaped steel plaque that may be attached to the fabric layer 52 in the manner illustrated in FIG. 6. FIG. 9 illustrates an embodiment of the invention in which the object of ferrous material 60 is formed as a generally triangularly-shaped steel plate or sheet which is secured atop the fabric layer 52 of the hat bill 54 proximate the headband of the hat 50 at one corner of the bill 54.

All of the ferrous objects 56, 58, and 60 illustrated in FIGS. 6–9 must contain enough iron so that they are subject to the magnetic force of attraction exerted by the magnetic ball marker of the invention. Both surfaces of the ferrous objects 56, 58, and 60 are plated with a finishing film so that they will not rust and will not discolor the fabric layer 52 of the hat bill 54.

Figure 7:
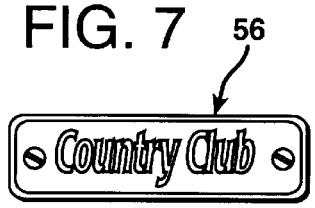
FIG. 7 is a detail plan view illustrating the ferrous object employed in the golf hat shown in FIG. 6.
Figure 11:
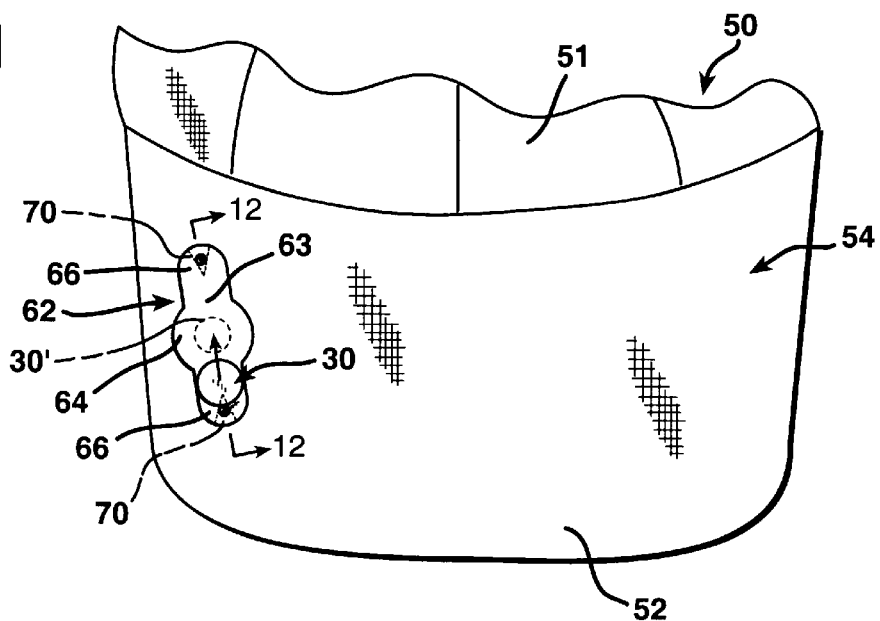
FIG. 11 illustrates a combination according to the invention employing the ferrous article shown in FIG. 10.
Figure 12:
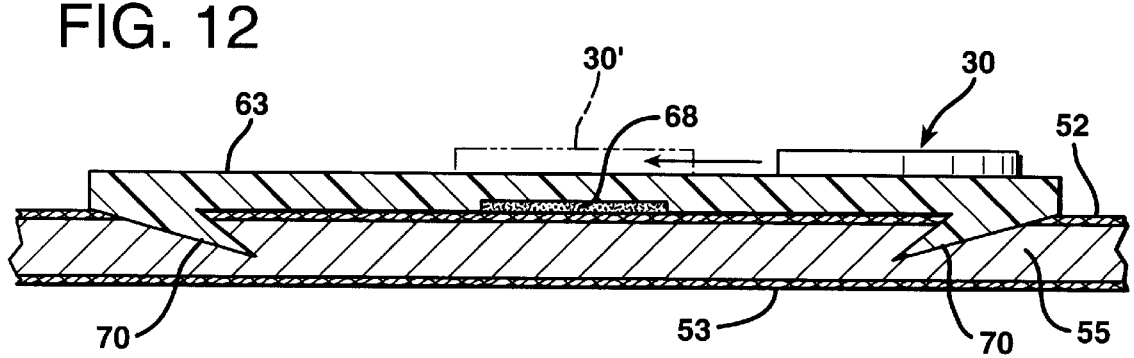
FIG. 12 is a sectional elevational detail taken along the lines 12—12 of FIG. 11.

The ball marker attraction device 62 differs from the objects illustrated in FIGS. 7, 8, and 9 in that the strip 63 employed can be formed of a nonferrous material, such as brass or plastic. The use of the ball marker attracting device 62 is illustrated in FIGS. 11 and 12. In the embodiment depicted in those drawing figures, the flat object formed of ferrous material is not the strip 63, but rather the flat, disc-shaped magnet 68 positioned therebeneath.

FIGS. 11 and 12 illustrate a further embodiment of an improved article of golf clothing according to the invention and employing the ball marker attracting device 62. As shown in FIGS. 11 and 12, the ball marker attracting device 62 of FIG. 10 includes a flat plastic strip 63 that is secured in a fixed position atop the hat bill 54 on the exposed surface of the fabric layer 52 in the manner previously described. However, the combination of elements illustrated in FIGS. 11 and 12 is further comprised of a second magnet 68 that is affixed in position relative to the plastic strip 63 and relative to the layer of fabric 52. Specifically, the plastic strip 63 is formed with a generally circular central region 64 and a pair of wings 66 extending in diametrically opposed directions therefrom. A circular depression is formed in the underside of the plastic strip 63 to a sufficient depth to receive at least a portion of the second magnet 68, which is visible in FIG. 12. The depression in the underside of the strip 63 may be formed by stamping and prevents any lateral movement of the second magnet 68 atop the fabric layer 52. The plastic strip 63 is secured to the hat bill 54 by a pair of prongs or spikes 70 that puncture the fabric cloth layer 52 at a sharp, acute angle.

The golf hat or cap 10 is formed with a cotton, wool, or synthetic fabric crown 51 surrounded by a hat band at its lower extremity. In the forehead region, a bill 54 is secured to the hat band and is constructed with a generally flat core 55, visible in the detail view of FIG. 12. The core 55 may be formed of fiberboard or some other material stiff enough to provide the bill 54 with a permanent shape. The flat, roughly crescent-shaped core 55 is wrapped with a sheet of fabric that forms a layer 53 on the underside of the bill 54 and an overlying fabric layer 52 on the upper, exposed surface of the bill 54.

The prongs 70 of the plastic strip 63 are angled into the structure of the hat bill 54. The prongs 70 penetrate through the upper fabric layer 52 and into the stiffening core 55 so as to hold the plastic strip 63 in a selected, fixed location atop the bill 54 of the hat 50. In addition to the anchored attachment provided by the prongs 70, attachment of the strip 63 to the hat bill 54 may be enhanced by the use of an adhesive between the underside of the strip 63 and the exposed surface of the fabric layer 52 directly therebeneath.

The ball marker attraction device 62 covers a predetermined area of the layer of fabric 52 on the hat bill 54. The second magnet 68 is located beneath the central, circular region 64 of the strip 63 and within the confines of the predetermined area covered by the strip 63. The second magnet 68 is sandwiched in between the strip 63 and the exposed side of the layer of fabric 52. As a consequence, if a magnetic golf ball marker such as the ball marker 30 or 10 is placed atop the hat bill 54 in contact, for example, with either of the wings 66, as illustrated in FIGS. 11 and 12, the ball marker 30 or 10 will move without assistance from a position laterally displaced from the central region 64 toward the center of the central region 64 directly above the second magnet 68. This action occurs due to the force of magnetic attraction exerted by the magnet 20 or 40 in the magnetic ball marker 10 or 30 and due to the presence of the second magnet 68 beneath the central region 64 of the strip 63. The second magnet 68 is disposed so that the polarity of its upwardly facing circular surface that resides in contact with the underside of the central region 64 of the steel strip 62 is of the opposite polarity from the polarity of the downwardly facing surface of the magnet 20 or 40 in the ball marker 10 or 30.

Thus, the ball marker 30 or 10, when placed atop the hat bill 54 in the vicinity of the strip 63 will scoot laterally from the position indicated at 30 in FIGS. 11 and 12 to the position indicated in phantom at 30'. The magnet thus centers itself directly atop and within the periphery of the central region 64 of the strip 63. Indeed, the force of magnetic attraction between the second magnet 68 and the magnet 20 or 40 of the ball marker is sufficiently strong so that the ball marker does not even need to contact the strip 63 at all in order for the magnetic ball marker to be drawn by magnetism into the position indicated at 30' in FIGS. 11 and 12.

The ball marker attraction device employed in an article of golf clothing according to the invention may be located externally on the article, such as the articles of head gear illustrated in FIGS. 6 and 11. Alternatively, however, the ball marker attracting device may be concealed from view.

Figure 13:
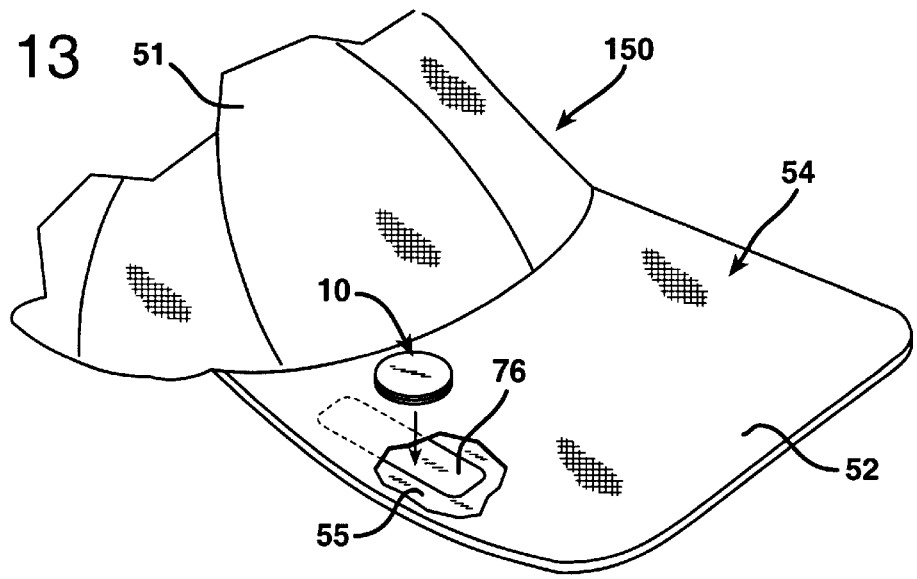
FIG. 13 illustrates still another alternative embodiment of a combination according to the invention.
Figure 14:
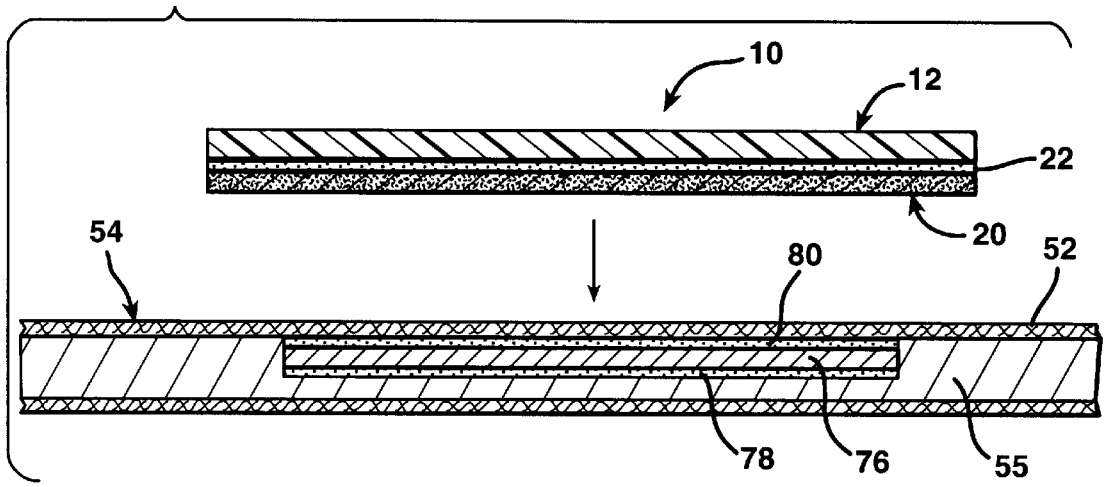
FIG. 14 is a sectional elevational detail showing a portion of the combination of FIG. 13.

FIGS. 13 and 14 illustrate a golf hat 150 constructed in the manner previously described. In the embodiment of FIGS. 13 and 14, the upper layer of cloth 52 on the upper surface of the hat bill 54 is a nonferrous sheet of material that conceals from view the object of ferrous material, which is a thin, relatively narrow steel strip 76. The hat 150 is modified during construction by the creation of a cradle or tray on the upper surface of the core 55 of the hat bill 54 at a selected location thereon. This shallow cavity is configured to snugly receive the steel strip 76 therewithin, as illustrated in FIG. 14. The steel strip 76 is maintained in position not only by the lateral constraints provided by the laterally surrounding structure of the core 55, but also by a lower layer of adhesive 78 that bonds the steel strip 76 to the core 55, and an upper layer of adhesive 80 that bonds the steel strip 76 to the concealed surface of the upper fabric layer 52 of the hat bill 54.

In the embodiment of FIGS. 13 and 14, a magnetic golf ball marker, such as the ball marker 10 or the ball marker 30, will be magnetically attracted to the steel strip 76 when moved into proximity thereto. Consequently, when the ball marker resides atop the fabric layer 52 near the steel strip 76, it will cling thereto for no visually apparent reason. This is because the strength of the magnet 20 or 40 on the underside of the ball marker 10 or 30 is strong enough to exert a sufficient magnetic force of attraction through the cloth layer 52 to hold the ball marker at a selected location on the hat bill 54, as determined by the location of the steel strip 76.

Figure 15:
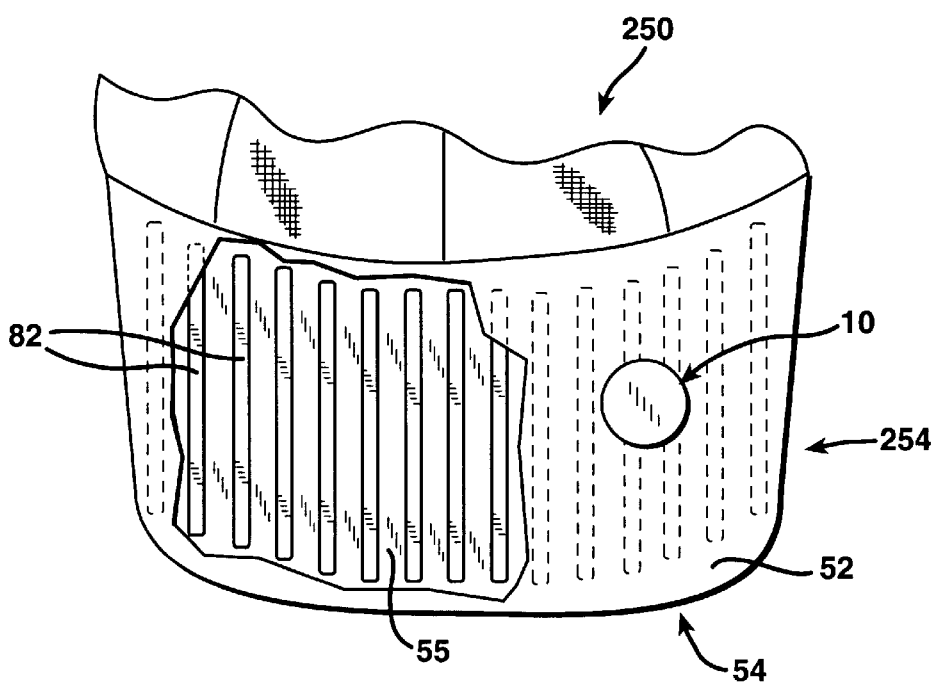
FIG. 15 is a top plan view of a combination of a magnetic ball marker with an article of clothing having ferrous objects embedded therein according to the invention.

An article of golf clothing according to the invention may be constructed so as to attract a magnetic ball marker to any number of different locations. FIG. 15 illustrates a golf hat 250 in which a plurality of trays or channels are formed in the core material 55 of the hat bill 254, all of which extend generally parallel to each other from locations proximate the hat band toward the opposite forward end of the hat bill 254. A separate metal strip or wire 82 is positioned within each of the cavities created in the upper surface of the hat bill core 55. These steel strips or wires 82 are secured in position within the hat bill 254 by adhesive in the manner described in the embodiment of FIGS. 13 and 14.

The upper fabric layer 52 of the hat bill 254 conceals the ferrous strips from view so that the presence of the strips 82 within the hat bill 254 cannot be detected by visual observation. Nevertheless, when a magnetic golf ball marker 10 or 30 according to the invention is placed atop the hat bill 254, it will cling thereto due to the force of magnetic attraction exerted by the ball marker magnet 20 or 40 upon the metal strip or strips 82 located directly therebeneath, as illustrated in FIGS. 14 and 15. In the embodiment illustrated in those drawing figures, the magnetic marker, such as the ball marker 10 or 30, will cling to the hat bill 254 of the hat 250 when placed at virtually any location on the fabric layer 52 of the hat bill 254.

Figure 18:
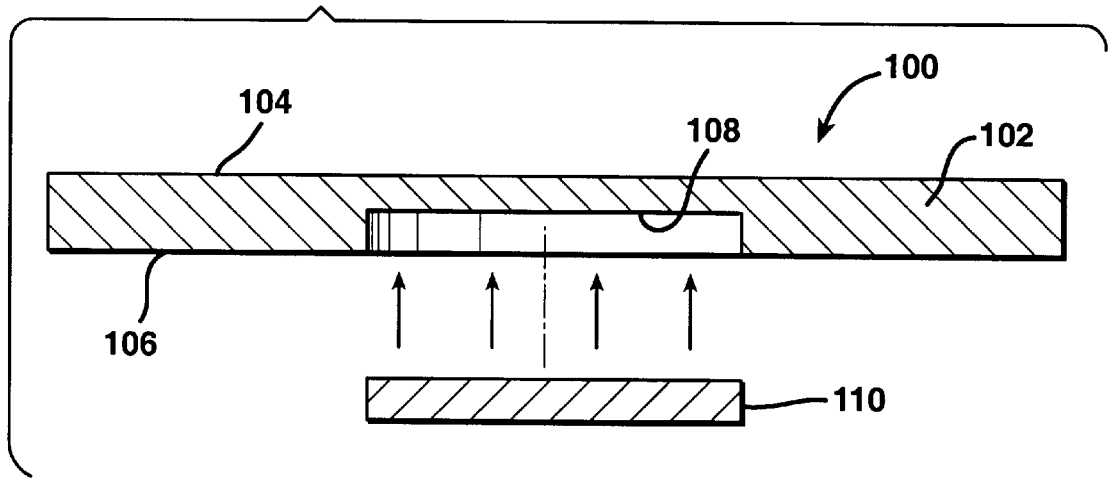
FIG. 18 is an exploded sectional elevational view of the magnetic ball marker shown in FIG. 17.

FIG. 18 illustrates another embodiment of a magnetic ball marker according to the invention. The magnetic ball marker 100 shown in FIG. 10 is formed of a flat slab of nonferrous material, such as brass or plastic, which is stamped to define a body 102. The upper surface 104 of the magnetically inert body 102 bears an indicia comparable to the indicia 16 of the ball marker 10 of FIG. 1. The undersurface 106 of the nonferrous body 102 has a central, disc-shaped cavity 108 defined therein. The magnetically inert body 102 is preferably formed from a material that is somewhat malleable, so that the cavity 108 can be defined by stamping a disc-shaped depression into the undersurface 106 of the body 102. Alternatively, the cavity 108 may be formed by milling out material from the body 102 at the center of the undersurface 106 using an end mill and lathe. Other conventional methods of forming the cavity 108 may also be employed.

The cavity 108 is created to accommodate and seat a small, flat, disc-shaped magnet 110. The diameter of the magnet 110 is just slightly greater than the diameter of the cavity 108, so that the magnet 110 can be permanently secured to the magnetically inert body 102 by force fitting it into the cavity 108.

Preferably, the outer diameter of the body 102 is either one inch or three-quarters of an inch. These are the standard sizes for golf ball markers that are widely utilized in the game of golf. The diameter of the cavity 108 is preferably about 11.98 millimeters and the depth of the cavity 108, as measure from the undersurface 106, is preferably about 0.62 millimeters. The overall thickness of the body 102, as measured at its periphery, is preferably between about 1.2 millimeters and 1.3 millimeters.

The magnet 110 preferably has a diameter of twelve millimeters and a thickness of 0.6 millimeters. As a consequence, when the magnet 110 is pressed into the cavity 108, as indicated by the directional arrows in FIG. 18, the interference fit between the outer diameter of the magnet 110 and the inner diameter of the cavity 108 creates a very slight inelastic deformation in the ball marker body 102 so that the magnet 110 is permanently locked in the cavity 108 without the use of an adhesive. In the magnetic golf ball marker 100, the magnet 110 is permanently seated in the cavity 108 and is laterally surrounded by the structure of the slab of nonferrous material forming the body 102.

Figure 16:
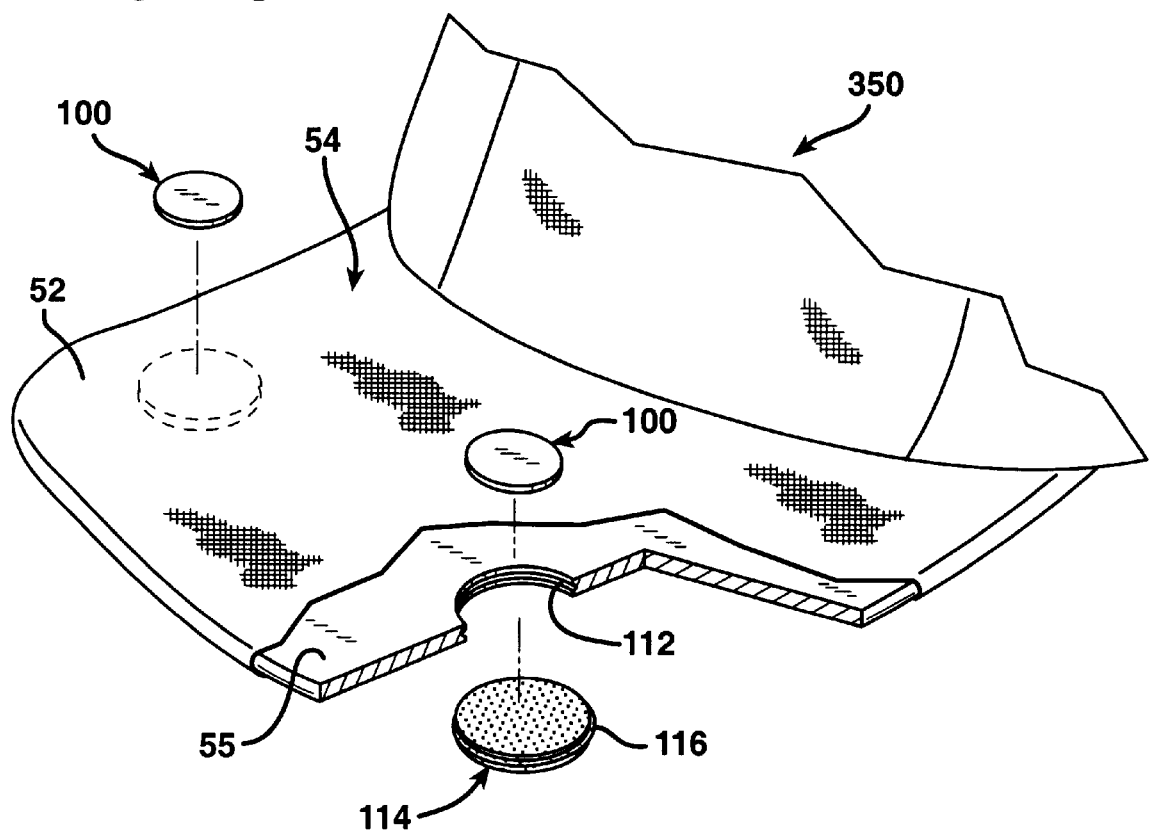
FIG. 16 is a perspective view that illustrates a different embodiment of a magnetic golf ball marker according to the invention in combination with an article of golf clothing.
Figure 17:
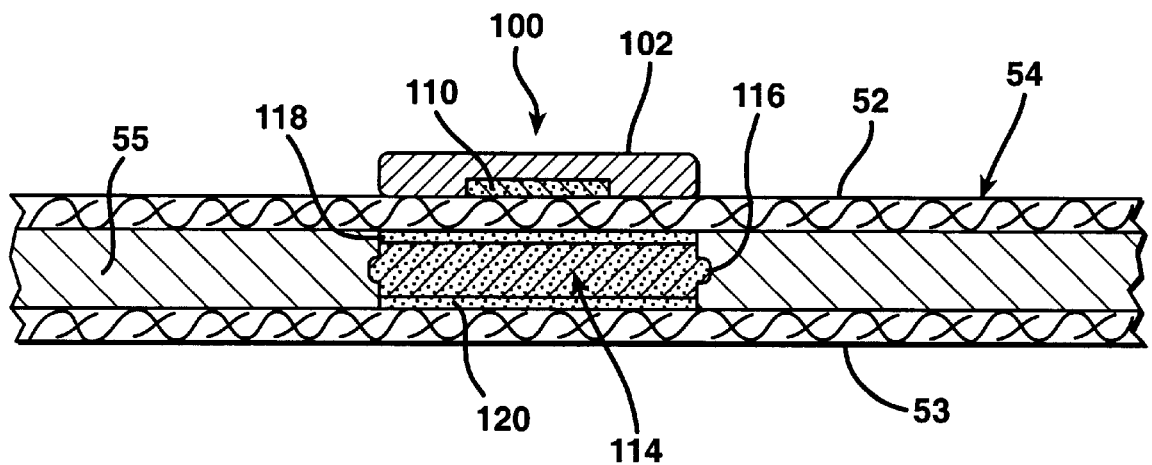
FIG. 17 is a sectional elevational detail of the combination of FIG. 16.

FIGS. 16 and 17 illustrate still another embodiment of an improved golf accessory according to the invention. As illustrated in those drawing figures, the stiff core 55 of the hat bill 54 may be formed with one or more generally disc-shaped positioning openings 112 therein. As with the hats 50, 150, and 250, the hat 350 is constructed with a bill 54 that has an upper fabric layer 52 and a lower fabric layer 53 that respectively reside atop and beneath the stiffer crescent-shaped core 55. The disc-shaped positioning openings 112 are formed with narrow, radially outwardly extending channels mid way between the upper and lower surfaces of the core 55. An object of ferrous material, namely a thin, generally disc-shaped steel wafer 114 is employed which has a radially outwardly projection rib 116 on its periphery. A separate steel wafer 114 is pressed into each of the generally disc-shaped positioning openings 112 so that the rib 116 of each wafer 114 fits into the corresponding radial channel defined about the inner wall of each positioning opening 112.

The wafer 114 has a thickness slightly less than the thickness of the hat bill core 55. Layers of adhesive 118 and 120 are applied to the upper and lower surfaces of the steel wafer 114, respectively. Each generally disc-shaped positioning opening 112 in the stiff, flat interior core 55 serves as a positioning opening for attracting a magnetic golf ball marker at a selected location within the hat bill 54. A steel wafer 114, is mounted in each positioning opening 112 where it is permanently secured to the hat bill 54 by the interaction between the radial rib 116 and corresponding groove in the core material 55, and by the adhesive layers 118 and 120 that bond the wafers 114 to both the concealed side of the overlying upper fabric layer 52 and the concealed side of the underlying fabric layer 53. The hat bill core 55, with the steel wafers 114 immobilized therewithin, is encapsulated between the upper fabric layer 52 and the lower fabric layer 53.

As illustrated in FIG. 16, when a magnetic ball marker such as the ball marker 100 is moved into the proximity of any of the steel wafers 114, the force of magnetic attraction exerted by the magnet 110 will draw the ball marker 100 onto the fabric layer 52 directly above the closest concealed wafer 114. In the embodiment of FIGS. 16 and 17, a magnetic ball marker according to the invention will thereby adhere to the hat bill 54 at the selected locations as determined by the positioning openings 112 without any visually detectable means of attachment. The ball markers 100 can thereby be carried on the golf hats 350 in a very convenient and readily accessible manner.

The magnet of any one of the embodiments of the different magnetic ball markers exerts a magnet field that acts through the layers of flexible fabric material, such as the fabric layers 52 and 53. The golf ball marker will thereby adhere to an article of clothing, such as the hat 350, on the exterior surface thereof when moved into proximity to any one of the wafers 114 of ferrous material located therewithin, unless it is dislodged therefrom by a force stronger than the magnetic field. A golfer may apply this force using his or her fingernail to merely lift the ball marker away from the cap bill 54. However, until or unless such a force is purposely applied, the magnetic ball marker will remain attached to the outer surface of the hat bill due to the force of magnetic attraction to the steel wafer 114 even if the hat is dropped, turned upside down, or otherwise subjected to manipulation.

The fabric layers 52 and 53 are each only a fraction of an inch in thickness, so that their presence does not materially attenuate the magnetic force of attraction exerted by the magnet 110 at either the exposed upper surface of the fabric layer 52 or at the exposed undersurface of the fabric layer 53 of the cap bill 54 either, for that matter. As a consequence, a significant magnet force is exerted through both of the fabric layers 52 and 53, both of which are in intimate contact with the steel wafers 114. The ball markers 100 can thereby be carried on the under surface of the hat bill 54, as well as upon the upper surface as illustrated.

Figure 19:
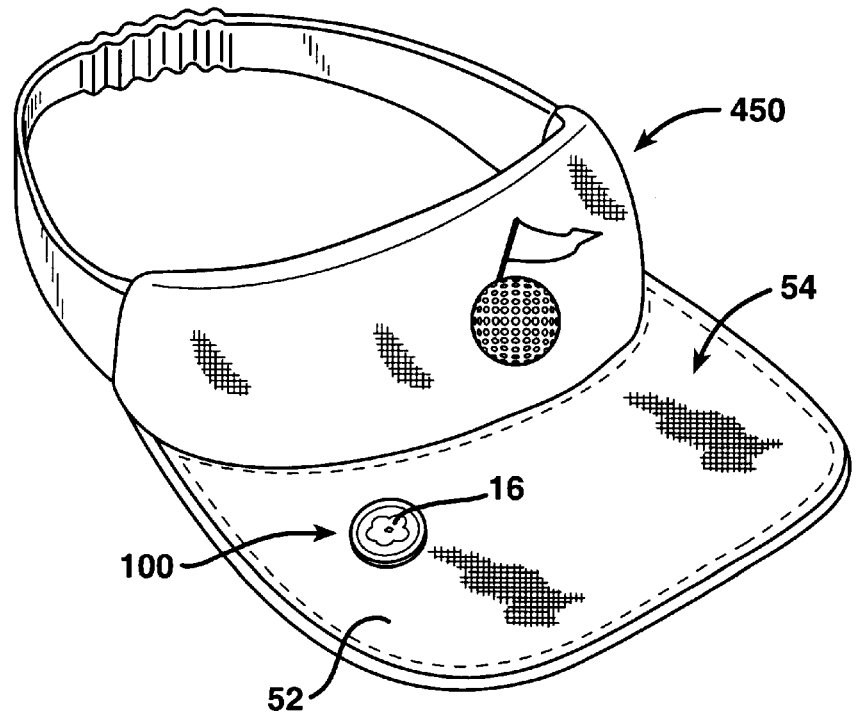
FIG. 19 is a perspective view illustrating the magnetic golf ball marker of FIG. 18 in combination with a golf sun visor.

While the magnetic ball marker of the invention has a wide variety of uses with many different of articles of golf clothing and accessories, its use is particularly attractive in combination with the articles of golf headwear, such as those illustrated. FIG. 19 illustrates a golf visor 450 which employs a hat bill 54 constructed in the same manner depicted and described in association with the hat 350 shown in FIGS. 16 and 17. As with the hat 350, the golf sun visor 450 has one or more thin, ferrous objects permanently secured in the visor bill 54 beneath an overlying fabric layer 52. When a magnetic golf ball marker, such as the golf ball marker 100 is located upon the exterior of the fabric 52. The magnet 110 of the ball marker 100 exerts a force of magnetic attraction. The ball marker 100 is thereby attracted toward the ferrous object embedded within the visor bill 54 of the sun visor 450 when moved in proximity to the ferrous object and clings to the visor bill 54, until or unless removed by a force that overcomes the force of attraction.

The invention is not limited to systems in which ferrous objects are incorporated into articles of golf clothing or golf accessories as manufactured. To the contrary, otherwise conventional articles of golf clothing or other accessories can be easily modified according to the invention.

Figure 20:
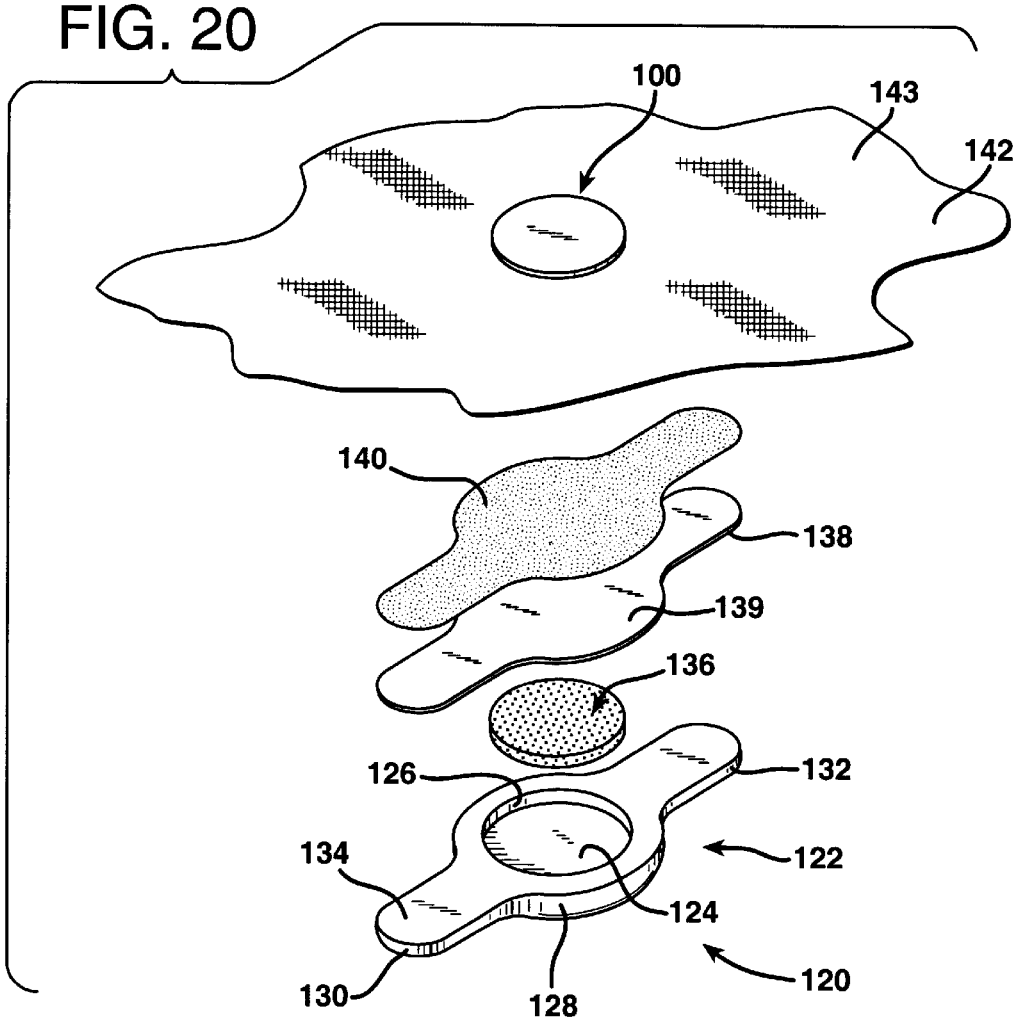
FIG. 20 is an exploded perspective detail illustrating a combination of the magnetic golf ball marker of FIG. 18 with a shallow tray containing an object of ferrous material mounted on a concealed side of a fabric layer of an article of golf clothing.
Figure 21:
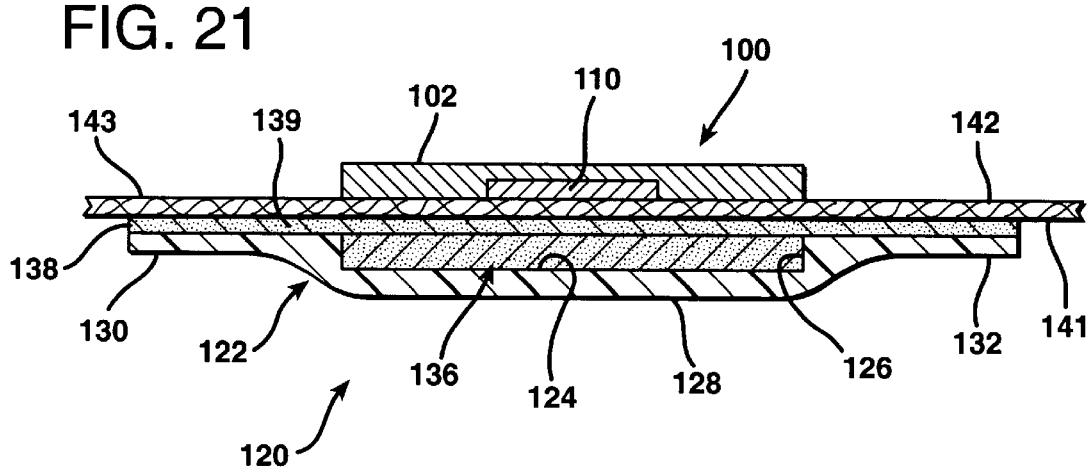
FIG. 21 is a sectional elevational view illustrating the magnetic adhesion of the ball marker to the article of golf clothing of FIG. 20.

FIGS. 20 and 21 illustrate an embodiment of the magnetic retention system which includes a ball marker attraction system 120 suitable for attachment to virtually any article of clothing or other fabric article utilized as a sporting or recreational accessory. The ball marker attraction system 120 is a patch that includes a shallow tray 122 formed as a molded structure of flexible plastic, such as polyvinyl chloride. The tray 122 is molded to include a flat, circular floor 124 and a short, cylindrical surrounding wall 126 extending upwardly about the perimeter of the floor 124. The tray 122 defines an enlarged, central, generally disc-shaped portion 128 from which a pair of wings 130 and 132 extend in opposite directions. The tray 122 has an outwardly facing flat surface 134 on its upper side surrounding the tray cavity and extending about the periphery of the central region 128 and across the wings 130 and 132. The flat surface 134 surrounds the cavity formed within the tray 122.

The ball marker attraction system 120 also includes a disc-shaped ferrous object, which may be a flat steel wafer 136 that fits snugly into the cavity formed within the cylindrical wall 126 and atop the floor 124. The steel wafer 136 is thereby disposed within the cavity of the tray 122. The wafer 136 may be formed of an iron, steel, or any other material that is attracted by the force of magnetism.

The ball marker attraction system 120 also includes a thin, plastic film 138 that covers the entire flat surface 134 and also at least the periphery of the outwardly facing circular upper surface of the steel wafer 136 located within the cavity of the tray 122. The plastic film 138 may be adhesively bonded to the flat surface 134 and steel wafer 136, or it may be solvent welded or sonic welded to the flat surface 134. In either case the steel wafer 136 is entrapped between the tray 122 and the overlying film 138. The outwardly facing surface 139 of the plastic film 138 forms an attachment surface for the patch formed by the combined structure of the film 138, the steel wafer 136, and the tray 122.

The magnet retention system 120 also includes a layer of adhesive 140 spread across the outwardly facing patch attachment surface 139. The adhesive layer 140 establishes a firm, adhesive bond with the concealed side 141 of a layer of fabric 142 of an article of golf clothing, as illustrated in FIG. 21.

To prevent premature contact of the adhesive layer 140 with any surface other than the concealed surface 141 of the layer of fabric 142 at a predetermined desired position of attachment thereon, the adhesive layer 140 is initially covered with a conventional disposable film (not shown), the undersurface of which is coated with a release agent. The release agent faces the adhesive layer 140 and permits only a light adhesive bond between the protective film and the adhesive layer 140. When the ball marker attraction system 120 is to be attached to a layer of fabric 142, the protective film coated with release agent is stripped from the adhesive layer 140 and the adhesive layer 140 is pressed into contact with the concealed surface 141 of the fabric layer 142 at a desired position of attachment thereto.

Once the ball marker attraction system 120 has been attached to the fabric layer 142, any magnetic ball marker according to the invention, such as the magnetic ball marker 100 illustrated in FIGS. 20 and 21, will be attracted to the steel wafer 136 through the structure of the fabric layer 142, the adhesive layer 140, and the plastic film 138. The magnetic force of attraction is sufficient to firmly but releaseably hold any magnetic ball marker, such as any one of the magnetic ball markers 10, 30, or 100, in contact with the outer, visually exposed surface 143 of the fabric layer 142.

The magnetic field of the ball marker magnet 20, 40, or 110 easily acts through both the adhesive layer 140 and the plastic film 138 to exert a sufficient magnetic force upon the steel wafer 136 to hold the ball marker firmly in position in coaxial alignment with the steel wafer 136. The permanent magnet in the ball marker resides in contact with the exposed surface 143 of the fabric material 142 to hold the ball marker in registration with the patch 120 and on the exposed side 143 of the fabric layer 142 thereof opposite the concealed side 141 to which the ball marker attraction system 120 is fastened.

The patch formed by the ball marker attraction system 120 may be secured to virtually any article of golf clothing having a fabric layer thin enough to allow the magnet in the ball marker to closely approach the ferrous article embedded in the patch 120. The ball marker attracting patch 120 may thereby be fastened to the inner surface of a crown of a golf hat. For example, it may be placed against the concealed surface of the forehead area of the hat crown or between the fabric of the crown and the hatband of the hat. The patch 120 may also be applied to a golf shirt, a golf towel, and to other golf accessories having a thin layer of material.

Numerous other applications of the magnetic ball marker system of the invention will be come readily apparent to those familiar with the game of golf. For example, flexible rubber discs in which magnetized iron or iron oxide particles are embedded, or hard magnetized wafers of rubber in which magnetized iron or iron oxide particles are embedded may be utilized as permanent magnets in place of the ferrous metal magnetic discs illustrated. Accordingly, the scope of the invention should not be construed as limited to the specific embodiments illustrated, as other forms of the invention will become readily apparent in view of the disclosure herein.

I claim:

1. An improvement to a golf accessory formed with an exposed layer of fabric comprising a flat, thin object formed of ferrous material attached to and concealed by said exposed layer of fabric at a selected location thereon, and a detached golf ball marker including a permanent magnet permanently incorporated therein, whereby the magnetic force of attraction of said magnet acts through said exposed layer of fabric to hold said golf ball marker against said exposed layer of fabric at said selected location when moved into proximity thereto.

2. An improved golf accessory according to claim 1 wherein said golf accessory is an article of headwear.

3. An improved golf accessory according to claim 2 wherein said article of headwear has a bill formed of a stiff, flat interior core having a positioning opening therethrough at said selected location, and said core is located beneath said exposed layer of fabric, and said object formed of ferrous material is mounted in said positioning opening where it is permanently secured to said bill.

4. An improvement to an article of golf clothing comprising a flat, thin object of ferrous material attached to said article of clothing at a selected location thereon, wherein said article of golf clothing includes a layer of nonferrous sheet material that conceals said object of ferrous material from view at said selected location, and a detached golf ball marker that has a nonmagnetic body and a magnet permanently attached to said nonmagnetic body, whereby said magnet draws said golf ball marker toward said object of ferrous material and holds said golf ball marker against said layer of nonferrous sheet material when moved into proximity to said selected location.

5. An article of golf clothing according to claim 4 wherein said article of golf clothing is an article of headwear that has a visor with a stiff bill formed of said layer of nonferrous sheet material and said selected location is in said bill of said article of headwear.

6. In combination, an article of golf clothing formed of a flexible material having an exterior surface, a thin wafer of ferrous material permanently attached to said article of clothing beneath said exterior surface of said flexible material, and a golf ball marker formed of a body with a magnet permanently attached to said body, and said golf ball marker is placed in contact with said exterior surface of said flexible material so that said magnet exerts a magnetic field that acts through said flexible material, whereby said golf ball marker adheres to said article of clothing on said exterior surface of said flexible material when moved into proximity to said wafer of ferrous material unless dislodged therefrom by a force stronger than said magnetic field.

7. A combination according to claim 6 wherein said article of golf clothing is a hat.

8. A combination according to claim 6 wherein said article of golf clothing is a sun visor.

9. In combination, a golf accessory constructed of fabric having an exterior surface, a thin ferrous object permanently secured within the confines of said fabric, and a golf ball marker formed of a magnetically inert body having a magnet permanently secured thereto and said golf ball marker is located upon said exterior surface of said fabric and said magnet of said ball marker exerts a force of attraction, whereby said ball marker is attracted toward said ferrous object and remains secured in place on said exterior surface of said fabric when moved into proximity to said ferrous object until removed by a force that overcomes said force of magnetic attraction.

10. A combination according to claim 9 wherein said golf accessory is formed as an article of headwear.

11. In an article of golf clothing having at least one layer of fabric with a visually exposed side and an opposite concealed side, the improvement comprising at least one flat object formed of ferrous material secured in position to said layer of fabric at a selected, fixed location thereon, and a ball marker formed of a body and a magnet permanently secured to said body, whereby when placed near said fixed location of said layer of fabric, said ball marker is magnetically held to said object of ferrous material by the force of magnetic attraction between said magnet of said ball marker and said object of ferrous material.

12. An article of golf clothing according to claim 11 wherein said object of ferrous material is secured atop said visually exposed side of said layer of fabric.

13. An article of golf clothing according to claim 12 wherein said object of ferrous material is comprised a second magnet fixed in position relative to said layer of fabric.

14. An article of golf clothing according to claim 13 further comprising a flat strip that covers a predetermined area of said layer of fabric and said second magnet is located between said flat strip and said exposed side of said layer of fabric and within the confines of said predetermined area.

15. An article of golf clothing according to claim 11 further comprising a plurality of objects formed of ferrous material as aforesaid, each of said objects of ferrous material being shaped as a long, narrow strip in contact with said concealed side of said layer of fabric.

16. In combination:
   an article of clothing including a layer of flexible fabric material having an exposed side and an opposite concealed side;
   a patch including:
   a. a shallow tray having a floor, walls projecting outwardly from said floor to define a laterally enclosed cavity;
   b. an object formed of a ferrous material located within said cavity; and
   c. an outwardly facing attachment surface surrounding said cavity;
   a layer of adhesive interposed between said attachment surface of said patch and said concealed surface of said fabric material, thereby joining said patch to said layer of fabric material with said cavity enclosed therebetween and with said object formed of ferrous material entrapped between said shallow tray and said concealed side of said layer of fabric material; and
   a golf ball marker having a magnet permanently attached thereto, whereby when said ball marker is positioned at said exposed surface of said layer of flexible fabric material proximate said object formed of ferrous material, and said magnet exerts a magnetic force of attraction through said layer of fabric material thereby holding said golf ball marker in contact with said exposed surface of said layer of fabric material proximate said object of ferrous material.

17. A method of carrying a golf ball marker in open display on a fabric golf accessory comprising: securing an object of material attracted by magnetism to a layer of fabric of said golf accessory, and placing a golf ball marker formed of a magnetically inert body and a permanent magnet permanently secured to said body near said object of material attracted by magnetism whereby a magnetic field produced by said magnet of said golf ball marker draws said golf ball marker toward said object attracted by magnetism and holds it relative thereto when said golf ball marker is moved into the vicinity of said object of material attracted by magnetism until an opposing force stronger than said magnetic field dislodges said golf ball marker from said layer of fabric.

* * * * *